United States Patent [19]

Stark

[11] Patent Number: 5,409,960
[45] Date of Patent: Apr. 25, 1995

[54] PENTANE ENERGY TRANSFER MEDIUM IN GAS CONVERSION

[75] Inventor: Thomas M. Stark, Morristown, N.J.

[73] Assignee: Exxon Research and Engineering Company, Florham Park, N.J.

[21] Appl. No.: 259,952

[22] Filed: Jun. 15, 1994

Related U.S. Application Data

[63] Continuation-in-part of Ser. No. 28,444, Mar. 9, 1993, abandoned.

[51] Int. Cl.$^6$ ............................ C07C 1/04; C07C 1/06
[52] U.S. Cl. .................................. 518/700; 518/712; 518/703
[58] Field of Search ......................... 518/700, 712, 703

[56] References Cited

U.S. PATENT DOCUMENTS

| 2,486,894 | 11/1949 | Watson | 518/712 |
| 4,258,006 | 3/1981 | Flockenhaus et al. | 518/712 |
| 4,539,016 | 9/1985 | Flockenhaus et al. | 48/197 R |

FOREIGN PATENT DOCUMENTS

| 2651567 | 5/1978 | Germany | 518/712 |
| 683516 | 11/1952 | United Kingdom | 518/712 |

Primary Examiner—Howard T. Mars
Attorney, Agent, or Firm—Jay Simon

[57] ABSTRACT

Pentane (or similar light hydrocarbon) is used in a gas conversion process to consume the exothermic heat of reaction in the Fischer-Tropsch process, and expanded to produce the energy to drive the air plant compressors.

9 Claims, 2 Drawing Sheets

PENTANE ENERGY TRANSFER MEDIUM IN GAS CONVERSION

CROSS REFERENCE TO RELATED APPLICATION

This application is a continuation-in-part of U.S. Ser. No. 028,444, filed Mar. 9, 1993, now abandoned.

FIELD OF THE INVENTION

This invention relates to the use of inert, condensible media, e.g., pentane, for removing heat from hydrocarbon synthesis reactions such as the Fischer-Tropsch process. More particularly, this invention relates to the use of a coolant that: (1) having a boiling point and vaporizing at a pressure higher than the reaction pressure, thereby eliminating the risk of contaminating the cooling system when leaks occur therein; (2) can be expanded, thereby producing useful work, and then recondensed, pumped and recycled to the hydrocarbon synthesis step.

BACKGROUND OF THE INVENTION

Fischer-Tropsch processes invariably use water/steam as the cooling medium for this exothermic process. Thus, boiling water is pumped through cooling tubes in the reactor. As the reaction proceeds and heat is generated, it is absorbed by the water converting it to steam and thereby using the latent heat of vaporization to control reactor temperatures. Fischer-Tropsch reactions, particularly on a commercial scale, require many, many cooling tubes, whether for fixed bed or slurry operations, for maintaining proper temperatures. Thus, the risk of a tube failure or weld leak is compounded significantly. In the event of a tube leak, the contents of the reactor are normally at a higher pressure than a boiling water/steam coolant and reactor contents will leak into the cooling system resulting in severe contamination and ultimately shut down of the process. While steam/water cannot be pressurized to greater pressures than the reaction process, because the temperature would be too high, even if it could, a leak of steam into the process will tend to deactivate the Fischer-Tropsch catalyst. Consequently, a medium that is inert to the process is required.

SUMMARY OF THE INVENTION

In accordance with this invention, an inert, condensible medium, boiling at a pressure at or above, preferably above, the reaction pressure is employed as the cooling medium for Fischer-Tropsch reactions. (For purposes of this invention, inert means inert with respect to the Fischer-Tropsch reaction.) By using a material such as pentane, for example, which vaporizes at or above Fischer-Tropsch reaction pressures, cooling tube leaks will not involve reactants or reaction products entering the cooling system. Rather, the pentane will leak out of the cooling tubes and into the reaction mixture where it will have no effect either on the cooling system or the Fischer-Tropsch process. In fact, n-pentane, for example, is a product of the Fischer-Tropsch process. Thus, the process makes hydrocarbons, such as $C_5+$ paraffins, and the process can thereby supply the cooling medium make up requirements.

In an embodiment of this invention, the Fischer-Tropsch process is carried out in a slurry phase reaction system, designed to maintain substantial isothermality across the reaction zone. In such a system, the hydrocarbon coolant passes through a plurality of cooling tubes disposed within the slurry reactor. Because slurry phase reactions involve substantial backmixing relative to fixed bed reactions, the reactant driving force for the slurry reaction is much more uniform than for fixed bed systems; and therefore, the heat release is more uniform across the reactor, tending more towards isothermality. For purposes of this invention substantial isothermality may be taken as less than about 50° C. temperature spread across the reactor, preferably less than about 40° C. temperature spread, more preferably less than about 20° C. temperature spread.

In a preferred embodiment, the high pressure vaporized coolant is expanded through a turbo-expander, for example, or any piece of equipment that can take advantage of the work energy available. The energy thereby produced is recovered and utilized in the Fischer-Tropsch process, but is preferably used to operate compressors, particularly air plant compressors for separating oxygen from nitrogen so the oxygen can be used to generate synthesis gas for use in the Fischer-Tropsch process.

DETAILED DESCRIPTION

The Fischer-Tropsch process is a well known process and operates at temperatures ranging from about 175°–400° C., preferably about 190° C. to about 275° C., and pressures of about 1 to 100 atmospheres, preferably about 10–40 atmospheres.

Essentially, the Fischer-Tropsch process converts synthesis gas, CO and hydrogen, in ratios ranging from about 1/1 to 4/1, preferably 1.5/1 to 2.5/1, to higher hydrocarbons, e.g., $C_2+$, preferably $C_5+$, over a Group VIII metal, preferably cobalt, supported catalyst. The cobalt may be promoted with a variety of materials, e.g., ruthenium, zirconium, rhenium, hafnium, titanium, etc. The catalyst support may vary widely and is usually selected from a group containing refractory metal oxides, e.g., silica, alumina, silica-alumina, titania, or zeolites.

The cooling medium must be inert, condensible, and at its boiling point is at a pressure greater than the reaction pressure. Suitable coolants are liquid paraffins (at room temperature) such as $C_4$ to $C_{10}$ normal, iso and cyclic: paraffins, olefins, substituted cyclic paraffins, e.g., methyl cyclohexane, low molecular weight silanes and silyl ethers, oxygenates silicone oils and their light analogs. Preferred materials are normal, iso, or cyclic paraffins, particularly $C_4$ to $C_7$ paraffins, particularly $C_5$–$C_6$ paraffins, e.g., n-pentane. More preferably, the coolant is a single compound, e.g., pentane or hexane and not a mixture of two or more compounds (a mixture requiring more complex condensing operations), and therefore, has a boiling point rather than a boiling range.

Figure 1:
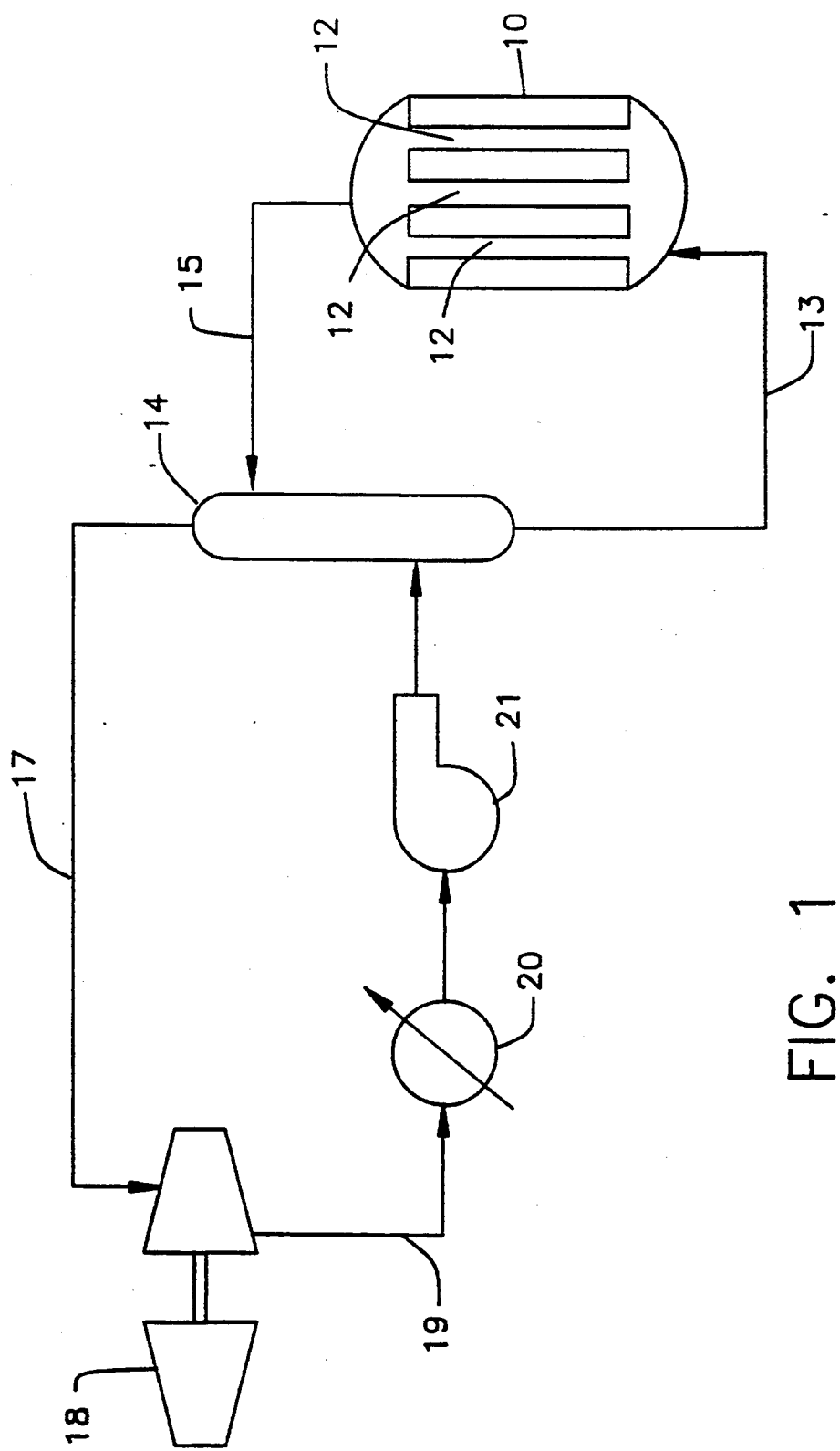
FIG. 1 shows a schematic arrangement for using pentane as the coolant for a slurry Fischer-Tropsch process.

Turning now to FIG. 1, reactor 10 may, for example, be operating at Fischer-Tropsch conditions of 15 atmospheres and 220° C. Liquid, high pressure pentane, e.g., about 25 atmospheres, stored in drum 14 is used to provide indirect cooling of the reactor by flowing through line 13 into the reactor and through cooling tubes 12, absorbing the heat of the slurry phase reaction and vaporizing. The vapor is recovered neat through line 15 (need not be separated from any other material in the reactor or in the cooing system) and through the overhead of drum 14 at about 24 atmospheres (allowing for some pressure drop in the lines) and at about 190° C. The vaporized pentane is sent by line 17 to expander 18 where the high pressure energy is recovered. The low pressure vapor leaving the expander, at about 105° C. and 1.5 atmospheres, is fed by line 19 to condenser 20 where the pentane is liquefied, i.e., by cold water or air, to about 50° C. and then pumped up to pressure in pump or compressor 21 and then back through the storage drum 14 and the reactor 10 for another cycle.

In a preferred embodiment, at least a portion and preferably a substantial portion of the energy recovered from the expander is used to drive compressors for an air plant which separates oxygen from nitrogen. Additionally, the energy can be used to drive other compressors or turbogenerators which produce electricity to be used in the process, e.g., for driving compressors, pumps, etc. The oxygen recovered from the air plant is used, preferably in combination with steam and natural gas or other hydrocarbons, e.g., lower hydrocarbons, such as $C_1$–$C_4$ alkyls, and preferably the presence of a reforming catalyst, e.g., 1–10 wt % nickel on alumina, to produce CO and hydrogen, preferably in a fluid bed process operating at about 1600° C.–2000° C. and 15–40 atmospheres. The CO and hydrogen are subsequently reacted in reactor 10 to produce hydrocarbons comprising $C_5+$ liquids.

Figure 2:
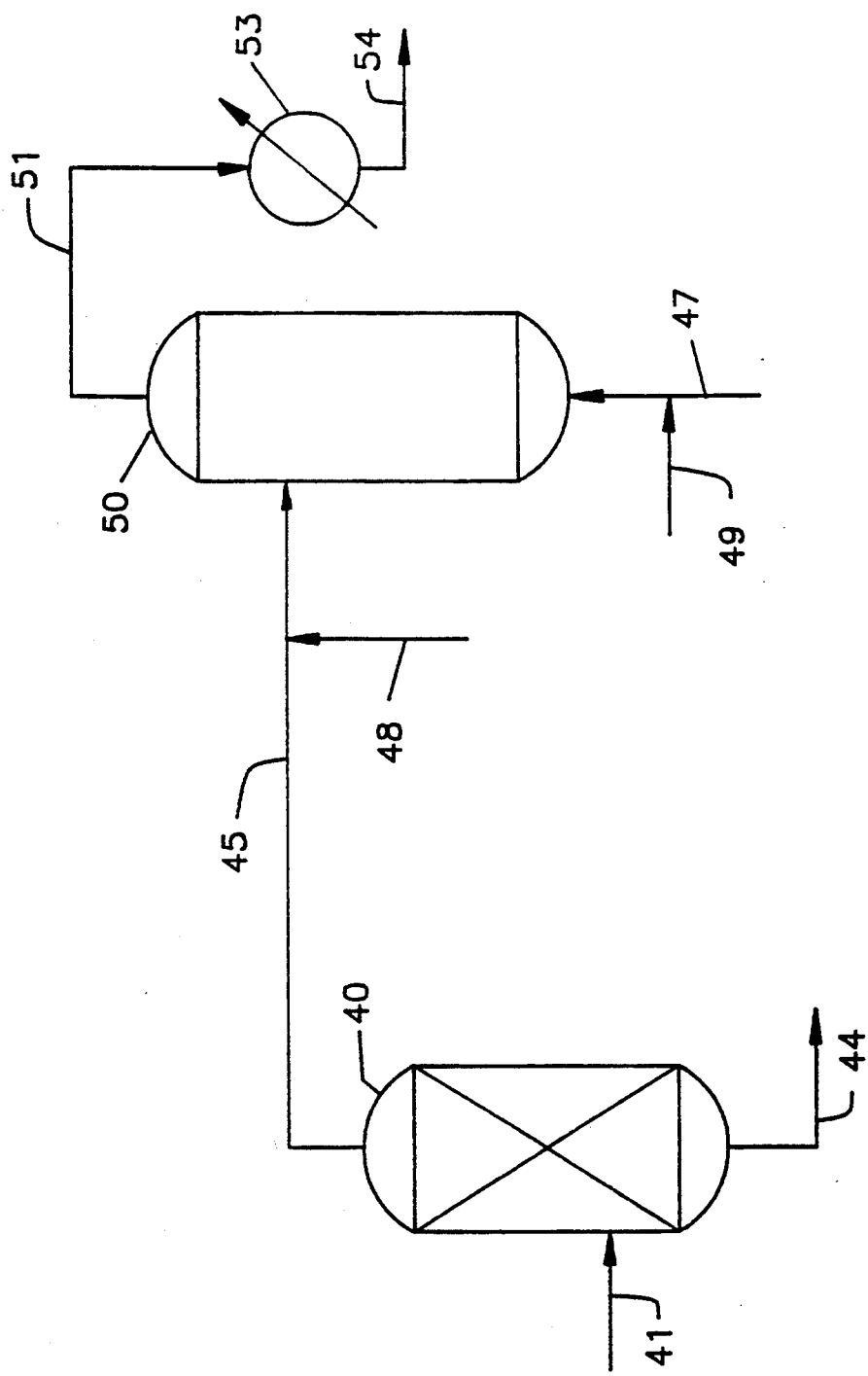
FIG. 2 shows a schematic for producing synthesis gas using an air plant.

This preferred embodiment is illustrated in FIG. 2 where the energy recovered from the expander is used to compress air entering the air plant 40 via line 41 where the compressed air is separated into nitrogen disposed of through line 44, and oxygen in line 45. The oxygen is fed to synthesis gas generator 50 where it is combined with natural gas, e.g., mostly methane, from line 47. Both the oxygen and the natural gas may be diluted with steam, lines 48 and 49. The synthesis gas is recovered from line 51 cooled in condenser 53 and forwarded to the Fischer-Tropsch reactor via line 54.

Essentially, operation of an air plant involves compressing and cooling air, first by water or ambient air, then by returning process streams ($O_2$, $N_2$ and "waste" mixtures of $O_2$ and $N_2$ as they are being warmed) and by reboiling the fractionation column, at which point the air is substantially condensed.

The air is then flashed into a tower, where it is fractionated and the products warmed against incoming air.

The use of non-corrosive hydrocarbons or silicone based fluids as cooling media eliminates the need for desalinization of water for a water/steam system. While a pentane system is not quite as efficient as a steam/water system, this is not a significant issue since excess steam is typically available in such systems; and the advantages of eliminating leak problems are manifest and, in the long run, the economics are more favorable.

What is claimed is:

1. A method for removing heat from a slurry Fischer-Tropsch hydrocarbon synthesis process reaction zone which comprises passing a cooling medium comprising a $C_4$–$C_{10}$ normal, iso- or cyclic paraffin liquid in cooling tubes in indirect heat exchange through the slurry reaction zone, thereby vaporizing the cooling medium at its boiling point, the cooling medium being inert for Fischer-Tropsch processes, condensible, and vaporizing at a pressure greater than the pressure in the reaction zone, and recovering the vaporized cooling medium neat.

2. The method of claim 1 wherein the reaction zone is at temperatures ranging from about 175° C.–400° C. and pressures ranging from about 1–100 atmospheres.

3. The method of claim 1 wherein the reaction zone is substantially isothermal.

4. The method of claim 1 wherein the cooling medium is a $C_4$–$C_7$ paraffin.

5. The method of claim 4 wherein the cooling medium is n-pentane.

6. The method of claim 1 wherein the vaporized cooling medium is expanded thereby creating energy, and a substantial portion of the energy is recovered and used in the hydrocarbon synthesis process.

7. The method of claim 1 wherein the vaporized cooling liquid is expanded, thereby creating energy and a substantial portion of the energy is recovered and used for driving compressors in an air plant.

8. The method of claim 7 wherein the air plant separates oxygen from nitrogen and the oxygen is reacted with a lower hydrocarbon to produce hydrogen and CO.

9. The method of claim 3 wherein the temperature spread across the reactor is less than 20° C.

* * * * *